United States Patent
Vasil et al.

(10) Patent No.: US 6,252,134 B1
(45) Date of Patent: Jun. 26, 2001

(54) TRANSFORMED WHEAT HAVING IMPROVED BREADMAKING CHARACTERISTICS

(75) Inventors: Indra K. Vasil; Vimla Vasil, both of Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 08/914,678

(22) Filed: Aug. 19, 1997

Related U.S. Application Data

(60) Provisional application No. 60/024,316, filed on Aug. 22, 1996.

(51) Int. Cl.⁷ ............................. A01H 1/00; C12N 15/82; C12N 15/87
(52) U.S. Cl. ..................... 800/278; 800/284; 800/290; 800/295; 800/298; 800/320.3; 800/320; 800/387; 435/468; 435/470; 435/419
(58) Field of Search ................................. 800/205, 250, 800/DIG. 9, DIG. 58, 278, 284, 287, 290, 295, 298, 320.3, 320; 435/468, 470, 419

(56) References Cited

FOREIGN PATENT DOCUMENTS

WO97/25419 7/1997 (WO).

OTHER PUBLICATIONS

Matzke and Matzke. Plant Physiol. 1995. vol. 107: 679–685.*
Napoli et al. The Plant Cell. 1989. vol. 2: 278–289.*
Weeks et al. Plant Physiol. 1993. vol. 102: 1077–1084.*
Anderson et al. Nucleic Acid Resaerch. 1989. vol. 17:461–462.*
Gordon–Kamm et al. The Plant CEll. 1990. vol. 2: 603–618.*
Altpeter, F., et al. (1996) "Integration and expression of the high–molecular–weight glutenin subunit 1Ax1 gene into wheat" Nature Biotechnology, vol. 14, pp. 1155–1549.
Thomas, M.S. et al. (1990) "Identification of an Enhancer Element for the Endosperm–Specific Expression of High Molecular Weight Glutenin" The Plant Cell, vol. 2, pp. 1171–1180.
Halford, N.G., et al. (1989) "Functional analysis of the upstream regions of a silent and an expresssed member of a family of wheat seed protein genes in transgenic tobacco" Plant Science, No. 62, pp. 207–216.
Robert, L.S. et al. (1989) "Tissue–Specific Expression of a Wheat High Molecular Weight Glutenin Gene in Transgenic Tobacco" The Plant Cell, pp. 569–578.
Blechl, A.E., et al. (1996) "Expression of a novel high–molecular–weight glutenin subunit gene in transgenic wheat" Nature Biotechnology, vol. 14, pp. 875–879.
Flavell, R.B., et al. (1989) "Genetic Variation in Wheat HMW Glutenin Subunits and the Molecular Basis of Bread–Making Quality" Bio/Technology, vol. 7, pp. 1281–1285.
Halford, N.G., et al. (1992) "Analysis of HMW glutenin subunits encoded by chromosome 1A of bread wheat (*Triticum aestivum* L.) Indicates quantitative effects on grain quality" Theor Appl Genet No. 83: 373–378.
Payne, P.I. (1987) "Genetics of Wheat Storage Proteins and the Effect of Allelic Variation on Bread–Making Quality" Plant Physiol. No. 38: 141–153.
Seilmeier, W., et al. (1991) "Separation and quantitative determination of high–molecular–weight subunits of glutenin from different wheat varieties and genetic variants of variety Sicco" Z. Lebensm Unters Forsch No. 192: 124–129.
Shewry, P.R. (1995) "Plant Storage Proteins" Biol. Rev. No. 70 pp. 375–426.
Shewry, P.R., et al. (1995) "Biotechnology of Breadmaking: Unraveling and Manipulating lthe Multi–Protein Gluten Complex" Bio/Technology, vol. 13, pp. 1185–1190.
Vasil, I.K. (1994) "Molecular Improvement of cereals" Plant Molecular Biology, No. 25:925–937.
Wrigley, C.W. (1996) "Giant proteins with flour power" Nature, vol. 381.

* cited by examiner

Primary Examiner—David T. Fox
Assistant Examiner—Ousama Zaphmout
(74) Attorney, Agent, or Firm—Saliwanchik, Lloyd & Saliwanchik

(57) ABSTRACT

Transgenic plants with increased amounts of high molecular weight glutenin subunits (HMW-GS) have improved breadmaking capability. A specific example of wheat (cv Bob White) transformed to express HMW-GS 1Ax1 is provided. In addition, advantageous uses of the 1Ax1 promoter are described.

25 Claims, 5 Drawing Sheets

TRANSFORMED WHEAT HAVING IMPROVED BREADMAKING CHARACTERISTICS

This application claims the benefit of U.S. Provisional Application 60/024316 filed Aug. 22, 1996

FIELD OF THE INVENTION

This invention pertains to the field of genetically transformed Graminae, particularly transformed wheat having improved breadmaking characteristics.

BACKGROUND OF THE INVENTION

The unique breadmaking characteristic of wheat flour is closely related to the elasticity and extensibility of the gluten proteins stored in the starchy endosperm, particularly the high molecular weight glutenin subunits (HMW-GS) which are important in determining gluten and dough elasticity. The quality of wheat cultivars depends on the number and composition of the HMW-GS present.

Prolamins are a novel group of storage proteins found in the endosperm of cereal grains (Shewry, 1995). The prolamins of wheat are divided into two groups, gliadins and glutenins. Together, they form gluten, a continuous proteinaceous network, during the mixing of wheat flour with water to make dough. The gluten proteins are the largest protein molecules found in nature (Wrigley, 1996). The elasticity (strength) and extensibility (viscosity) of the dough, critical for breadmaking, are closely related to glutenins and gliadins, respectively. These unique properties of wheat gluten, not found in the storage proteins of other cereals, are likely related to the enormous size of the glutenin polymers which have relative molecular masses ranging into the tens of millions (Wrigley, supra). Low (weak) gluten elasticity is responsible for the poor breadmaking qualities of wheat cultivars which otherwise have desirable agronomic properties. In such instances the mixing of flour from different cultivars is required in order to produce a blend suitable for breadmaking. Extensive biochemical and genetic investigations have shown that the breadmaking quality of wheat flour is determined particularly by the HMW-GS group of proteins. The HMW-GS are subdivided into high $M_r$ x-type and low $M_r$ y-type subunits. Two genes which are inherited as tightly linked pairs, encoding an x-type and a y-type subunit, are present on the 1A, 1B, and 1D chromosomes of hexaploid bread wheat (Payne, 1987). All cultivars of wheat, therefore, contain six HMW-GS genes, but only three, four, or five subunits are present, because some of the genes are silent (the 1 Ay gene is silent in all bread wheat varieties). The number and composition of HMW-GS present in a cultivar are closely related to the quality of its gluten. HMW-GS may represent up to 10% of the total seed protein, as each HMW-GS accounts for about 2% of the total extractable protein (Seilmeier et al., 1991; Halford et al., 1992). However, the close linkage of HMW-GS genes makes it difficult to manipulate them by traditional breeding methods (Flavell et al., 1989). Recent success in the transformation of wheat (Vasil, 1994), therefore, has provided an opportunity to try to improve the gluten quality of wheat by introducing additional copies of HMW-GS genes (Flavell et al., 1989; Shewry et al., 1995). Seeds of transgenic wheat (cv Bob White) containing a hybrid HMW-GS Dy10:Dx5 gene construct have just recently been shown to accumulate the hybrid HMW-GS to levels similar to those of the endogenous HMW-GS genes. Five HMW-GS-Ax2*, Bx7, By9, Dx5, and Dy10—are present in Bob White endosperm (Blechl and Anderson, 1996). The use of the hybrid gene construct was, therefore, necessary to discriminate between the native proteins encoded by the Dx5 and Dy10 genes, and the hybrid HMW-GS formed by the introduced Dy10 and Dx5 genes.

There exists a continuing need for wheat with improved breadmaking quality, and methods for creating such wheat. Therefore, it would be desirable to obtain wheat improved by transformation with heterologous HMW-GS genes which are expressed to yield improved breadmaking quality.

BRIEF SUMMARY OF THE INVENTION

This invention is methods for producing wheat with improved breadmaking characteristics by transforming wheat with heterologous HMW-GS genes. The subject invention is exemplified by the introduction of the HMW-GS 1Ax1 gene into the Bob White cultivar of wheat (*Triticum aestivum* L.), a cultivar in which the 1Ax1 gene is not present in nature, by the biolistic bombardment of cultured immature embryos. The 1Ax1 gene is known to be associated with good breadmaking quality but is not present in many cultivars (Halford et al., 1992; Payne et al., 1979), including Bob White (Blechl and Anderson, 1996). Of the 21 independent transformed lines selected, 20 expressed the selectable bar gene, and nine the 1Ax1 gene. The amount of HMW-GS 1Ax1 protein produced in the different transgenic lines varied from 0.6 to 2.3% of the total protein, resulting in up to 71 % increase in total HMW-GS proteins. The transgenic plants were normal, fertile, and showed Mendelian segregation of the transgenes. The accumulation of HMW-GS 1Ax1 was consistent and stable up to the R3 seed generation. This is the first time that anyone has created wheat in which more than five HMW-GS genes are expressed. Surprisingly, it has been discovered that additional heterologous genes above and beyond the five which are naturally expressed will express without silencing native gene expression. Accordingly, as exemplified herein, the subject invention enables those skilled in the art to predictably manipulate both the quantity and quality of HMW-GS by transforming wheat with heterologous HMW-GS genes of the artisan's choice which influence the breadmaking quality of wheat.

DETAILED DISCLOSURE OF THE INVENTION

Figure 4:
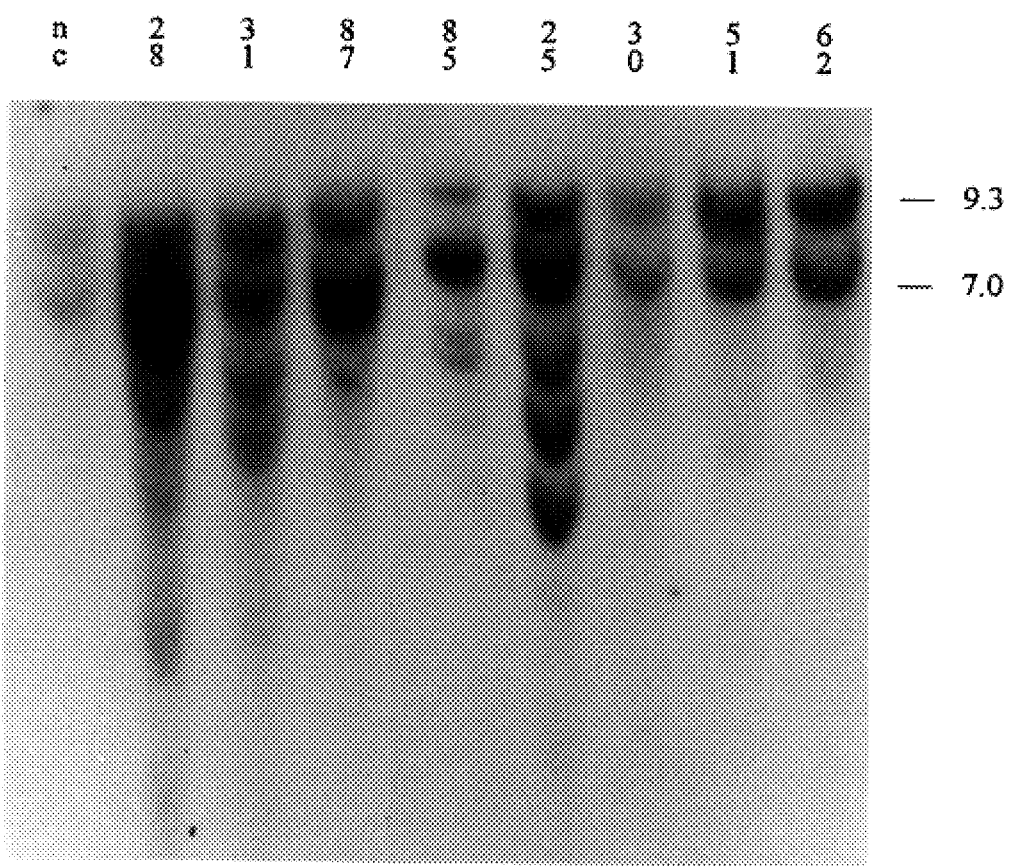
FIG. 4. Southern blot of genomic DNA (20 μg) of lines 28, 31, 87, 85, 25, 30, 51, and 62, and a non-transformed control plant (nc), restricted with XbaI and hybridized with the 1Ax1 probe. The sizes of the two hybridizing bands originating from endogenous HMW-GS genes are indicated in kb (right).
Figure 5:
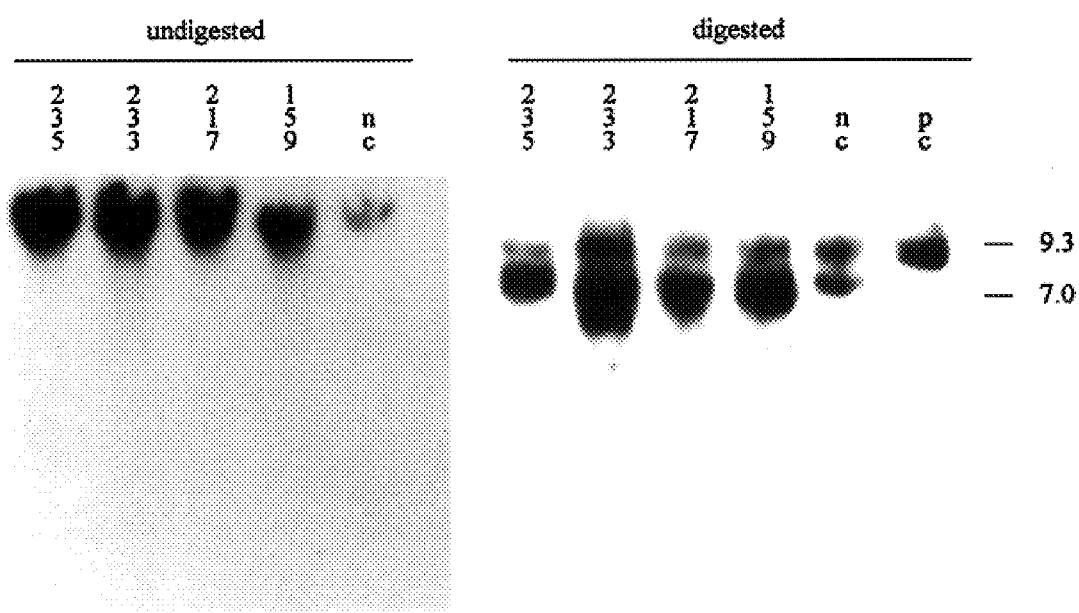
FIG. 5. Southern blot of genomic DNA of lines 235, 233, 217, and 159, a nontransformed control plant (nc), and DNA of plasmid pHMW1Ax1 (pc), were restricted with XbaI (right) or left undigested (left), and hybridized with the 1 Ax1 probe; 10 μg DNA for undigested samples, and 25 μg DNA for digested samples. The sizes of the two hybridizing bands originating from endogenous HMW-GS genes are indicated in kb (right).

The quantity of HMW-GS 1Ax1 present in the endosperm is positively correlated with dough elasticity/strength (Halford et al., 1992; Branlard, 1987). The manipulation of HMW-GS genes through traditional breeding, though possible, has been shown to be unpredictable, difficult, and complicated because of their close linkage (Flavell et al., 1989). The subject invention enables this barrier to the improvement of breadmaking quality of wheat to be overcome by the introduction and expression of additional HMW-GS genes by genetic transformation resulting in qualitative and quantitative changes in HMW-GS. The 1Ax1 gene is not present in the Bob White cultivar of wheat used as an example herein, making it possible to detect its transgenic expression in wheat by SDS-PAGE as a novel additional band, which is absent in the nontransformed control. A majority of the nine independently transformed lines expressing the HMW-GS 1Ax1 gene in R1 showed similar levels of expression in R2 seed extracts (Table 2). Densitometric analysis (Table 2) confirmed that the differences in the relative levels of HMW-GS accumulation between individual transgenic lines, including the amounts of HMW-GS 1Ax1, were stable through three generations. The bar and 1 Ax1 genes cosegregated in all the eight lines in which they were expressed. This indicates that integration occurred at a single locus in all the lines expressing 1Ax1 and bar, both of which were inherited in a Mendelian fashion in all but two lines (25 and 87). Integration of transgenes at single as well as multiple loci in the genome of cereal species has been described (Christou et al., 1989; Spencer et al., 1992; Srivastava et aL, 1996). Southern analysis of eight of the nine lines expressing HMW-GS 1Ax1 suggests that the 1Ax1 transgene is integrated in multiple copies in all the lines (FIGS. 4, 5). Thus far, eight lines have been identified as homozygous in R2. The expression of the transgene was maintained in successive generations in all lines. The amount of transgenic protein produced varied depending on the individual line, from 0.6 to 2.3% of the total extracted protein. The high level of expression of the introduced 1Ax1 gene, and its stability through at least three generations, suggests that the native HMW-GS gene promoter can be used effectively for the expression of transgenic proteins in the endosperm tissue of wheat and other cereals. Accordingly, use of the 1Ax1 promoter to drive expression of heterologous DNA segments encoding proteins is within the scope of the subject invention. Although scanning densitometry of SDS-PAGE does not provide precise quantitative data, it is nevertheless useful in assessing the effect of introduced HMW-GS genes. The methods taught herein resulted in an increase of up to 71% in total HMW-GS after introduction of the 1Ax1 gene. Surprisingly, the results demonstrate that in most of the lines the accumulation of the transgenic subunit 1Ax1 was not at the expense of the other HMW-GS (although lines 85 and 233 showed only a moderate level of 1Ax1 expression, it was nonetheless at the expense of other HMW-GS, so that the total HMW-GS level was in the range of the nontransformed control).

The subject invention concerns methods for enhancing and increasing the breadmaking characteristics of plants, such as wheat, through the transformation of the plants with genes encoding HMW-GS polypeptides. The subject invention also concerns the transformed and transgenic plants, plant material, and seeds having HMW-GS transgenes, or fragments or variants thereof. In a preferred embodiment, multiple copies of the HMW-GS transgene are integrated into the genome and expressed in the plant cell. The subject invention also encompasses bread and the like prepared from plants and seeds of the present invention.

It is therefore clear that, according to these teachings, the skilled artisan is enabled to increase the total number of HMW-GS genes, and thus the amount of HMW-GS accumulated, resulting in improved breadmaking quality. Further, the subject invention provides the opportunity to routinely manipulate the composition of HMW-GS, and thus its effect on breadmaking quality, by the introduction into wheat and other plants/cereals of genes mutated by means well known in the art to cause alterations in the structure of HMW-GS. In addition, HMW-GS genes can be altered by means well known in the art to add nucleotides (by insertion at restriction enzyme sites, for example) or to remove nucleotides (by use of Bal31 exonuclease, for example) to yield a variant or fragment which encodes a protein according to the teachings herein.

Thus, by following the teachings herein, the skilled artisan is provided the means and expectation that the HMW-GS 1Ax1 gene, or any other HMW-GS gene associated with good breadmaking quality, can be stably integrated, expressed, and inherited as a single dominant locus in the wheat genome following Mendelian inheritance. The following examples specifically show that, under the control of its native HMW-GS promoter, substantial amounts of HMW-GS 1Ax1, novel for the Bob White cultivar of wheat, are produced. These examples illustrate that one of ordinary skill in the art can predictably and routinely alter the composition of the wheat endosperm, and hence its suitability for human and industrial use, by the introduction of relevant HMW-GS genes by transformation according to the teachings herein. Similarly, the composition of maize, rice, and other cereals can be altered as taught herein and according to known transformation and selection techniques. It should be understood that methods of transformation other than the method specifically exemplified herein can be used in the methods of the subject invention and are contemplated within the scope of the invention.

Following are examples which illustrate procedures for practicing the invention. These examples should not be construed as limiting. All percentages are by weight and all solvent mixture proportions are by volume unless otherwise noted. The methods disclosed in each of the cited references are incorporated herein by reference, and in particular where noted.

EXAMPLE 1

Wheat Transformation and Plasmids

Transformation was carried out by bombardment of immature embryos of *Triticum aestivum* L. (cv Bob White) in a biolistic particle acceleration device (PDS1000/He, Bio-Rad) as described previously (Taylor et al., 1993; Vasil et al., 1993; Altpeter et al., 1996; methods of which are incorporated herein by reference). The plasmids pAHC25 and pHMW1Ax1 were mixed in approximately 1:1 molar ratio (5 µl of each DNA) for cotransformation. The plasmid pAHC25 contains the selectable bar gene and the GUS reporter gene (uidA), both under the control of the maize ubiquitin promoter (Vasil et al., 1993; Altpeter et al., 1996; Christensen and Quail, 1996). The plasmid pHMW1Ax1 contains the HMW-GS 1Ax1 gene of wheat whose expression is driven by its own endosperm specific promoter (Halford et al., 1992). Transgenic lines were selected on a bialaphos containing medium as described (Altpeter et al., 1996). A total of 21 independent transgenic wheat lines (20 expressing PAT) were obtained from 7650 embryos (in nine experiments), under suboptimal bombardment and selection conditions, giving an overall transformation frequency of 0.3%.

EXAMPLE 2

Cotransformation and Expression of HMW-GS 1Ax1 and bar

Figure 1:
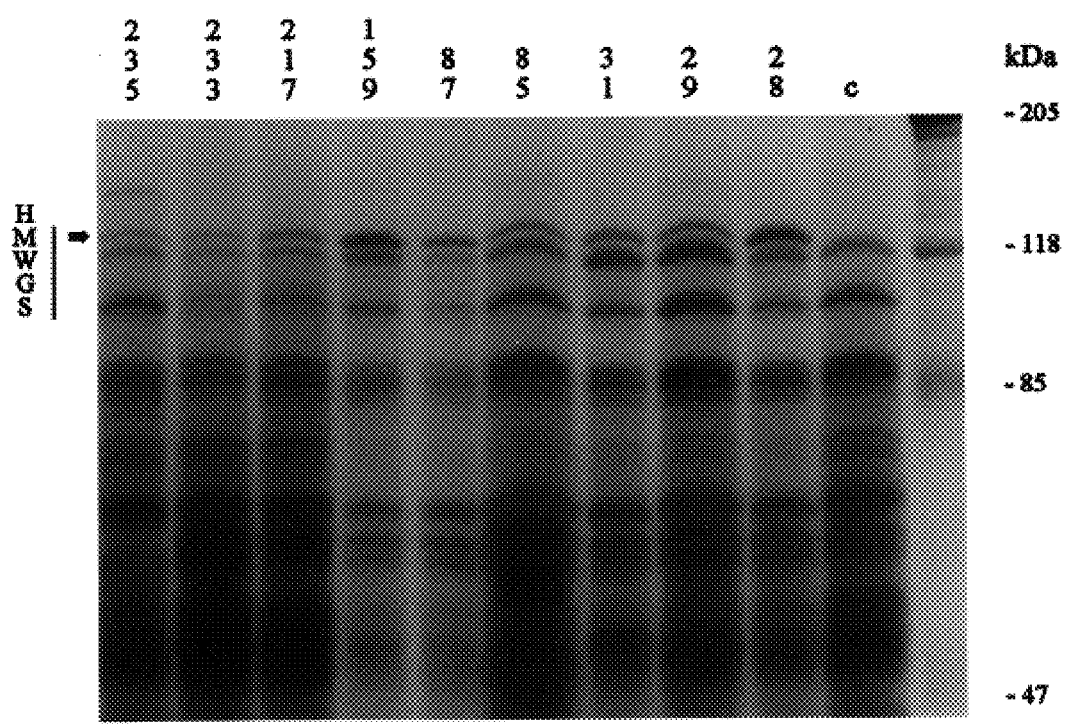
FIG. 1. SDS-PAGE of proteins from single R2 seeds of wheat cultivar Bob White transformed with the gene encoding HMW-GS 1Ax1. The bar indicates the location of HMW-GS subunits; the arrows mark the position of subunit 1Ax1. Numbers at the top correspond to the nine individual transformed lines expressing the 1Ax1 gene. HMW-GS 1Ax1 is not present in nontransformed Bob White (lane c). Proteins smaller than 46 kDa are not shown. Protein molecular weight standards are shown on the right.
Figure 2:
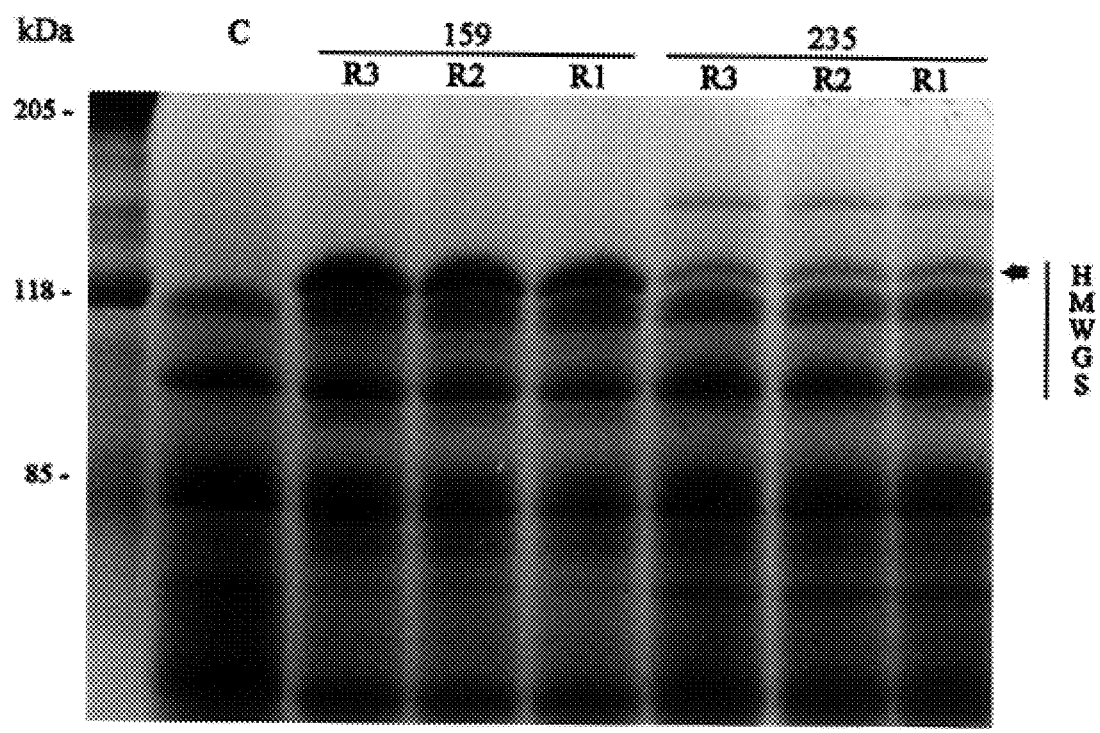
FIG. 2. SDS-PAGE of proteins from single seeds of line 159 (highest expresser) and line 235 (lowest expresser) showing uniformity of accumulation of HMW-GA 1Ax1 in R1, R2, and R3 seed. HMW-GS 1Ax1 is not present in nontransformed Bob White, lane C. Protein molecular weight standards are shown on the left.
Figure 3:
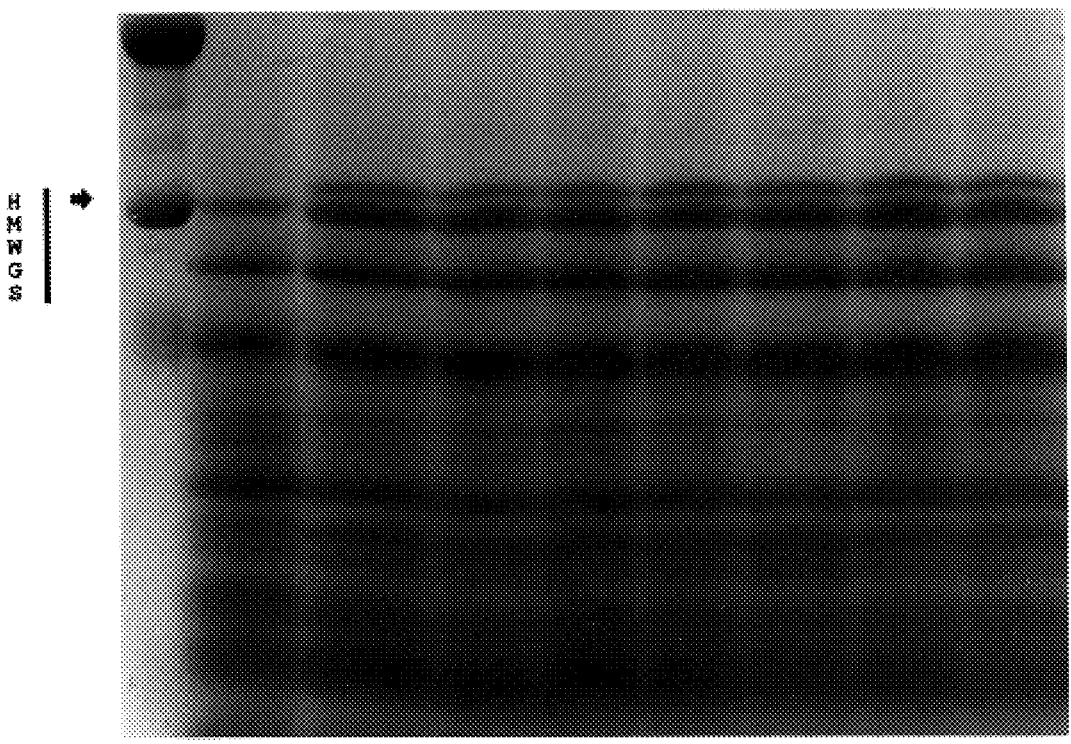
FIG. 3. SDS-PAGE of proteins from seven single seeds of line 29, homozygous for HMW-GS 1Ax1 gene expression in R2. The bar indicates the location of HMW-GS; the position of subunit 1Ax1 is shown by the arrow. HMW-GS 1Ax1 is not present in nontransformed Bob White (second lane from left). Protein molecular weight standards are shown in the left lane, as in FIG. 2.

Immature embryos of wheat cultivar Bob White were cotransformed withpAHC25 and pHMW1Ax1. Twenty independent transformed lines were identified based on determination of phosphinothricin acetyl transferase (PAT) activity. An additional line (line 85) was identified by Southern analysis (both the bar and 1Ax1 genes were present) in a separate experiment, carried out on 12 plants that survived selection on bialaphos but showed no PAT activity. Plants were transferred to soil in less than three months after culture initiation. Each of the 21 transformed lines was fully fertile and produced R1 seed. Total proteins were extracted individually from eight mature R1 seeds of each line and analyzed by SDS-PAGE for the accumulation of the transgenic HMW-GS 1Ax1. As shown in FIGS. 1–3, HMW-GS 1Ax1 protein is not present in control Bob White seeds (control lane). Therefore, the presence of the transgenic 1Ax1 subunit was clearly distinguishable in nine lines (two of these are shown in FIG. 2), with the protein banding at ca. 126 kDa relative to standard molecular weight markers. Of the 20 lines expressing PAT and cotransformed with pHMW1Ax1, eight also expressed the 1Ax1 transgene, giving a coexpression frequency of 40%.

EXAMPLE 3

PAT Assays

Following selection, primary transformants were identified by determination of PAT activity in leaf extracts by silica gel thin layer chromatography (Spencer et al., 1990, methods incorporated herein by reference), except that 2.0 µl of [$^{14}$C]acetyl-CoA 43.2 mCi/mmol (Sigma) was used as label. The products of the reaction corresponding to 25 µg of total protein were used from each sample.

EXAMPLE 4

Protein Analysis

Protein extracts were prepared by grinding mature dry seeds individually with a mortar and pestle. Ten to fourteen mg of the resultant flour from each seed was vortexed with 200 µl sample buffer (2% SDS, 5% β-mercaptoethanol, 0.001% Pyronin Y, 10% glycerol, 0.063 M Tris HCl pH 6.8) for 2 minutes and incubated for 2 hours on a rotary shaker at 250 rpm. The extracts were centrifuged (10 minutes, 14,000 rpm) and the supernatant boiled for 5 minutes to denature the protein. The proteins were separated by SDS-PAGE (Laemmli, 1970); 20 to 30 µl of each sample was loaded in 13 cm gels containing 10% (w/v) acrylamide, 0.8% (w/v) bis-acrylamide and run until the dye front had reached the bottom of the gel, so that the total extracted protein remained on the gel and the 1Ax1 band was resolved from the rest of the HMW-GS which were not complete separated from each other. The gels were first fixed in the staining solution without dye for 0.5 to 1 hour and then stained in Coomassie Brilliant Blue R-250 for 4 to 6 hours (Neuhoff et al., 1988). Protein bands were visualized by destaining in an aqueous solution of 5% methanol and 7% acetic acid (vol/vol) until a clear background was obtaned. Gels were stored in a 7% aqueous acetic acid solution (vol/vol). Stained gels were scanned using an Alpha Innotech (San Leandro, CA) IS-1000 Digital Imaging System. Lane and peak values were corrected by interband background subtraction. Background intensity was determined for each individual lane from the top of each HMW-GS 1Ax1 band at approximately 140 kDa. The amount of HMW-GS 1Ax1 present was calculated relative to the corrected lane value or the corrected HMW-GS value. To calculate the total HMW-GS level, the protein contents of each lane were normalized.

EXAMPLE 5

DNA Analysis

Genomic DNA was isolated from the leaves of PAT-positive plants by the CTAB method (Lassner et al., 1989, methods incorporated herein by reference). Purified DNA (20 to 25 µg) was digested withXbaI, electrophoresed in 0.8% agarose gel, and blotted on Hybond-N membrane (Amersham). The probe for hybridization consisted of the 2.2 kb fragment from the coding region of the HMW-GS 1Ax1 gene, derived after an EcoRI and HindIII digest of pHMW1Ax1, using the random primer labelling kit (GIBCO-BRL). Hybridization was performed at 65° C. for 24 hours, and signals were visualized by autoradiography.

EXAMPLE 6

Segregation Analysis

To determine the segregation ratios of transgene bar in the R1 generation, 20 mature embryos from each of the 21 transgenic lines were germinated on a medium supplemented with bialaphos: half strength MS-salts and vitamins (Murashige and Skoog, 1962; methods incorporated herein by reference) supplemented with 15 g/l sucrose, 2.5 g/l gelrite, and 3 mg/l bialaphos (added filter sterilized after autoclaving), pH 5.8 (B3 medium). The expression of the unselected 1Ax1 transgene was assessed in each of the successive generations and only the lines expressing the gene were carried on to the next generation. Lines homozygous for bar were identified from R2 seeds, by testing the germinability of 20 embryos from up to 12 R1 plants of all HMW-GS 1Ax1 accumulating lines on B3 medium. Ten seeds of each homozygous bar line were analyzed individually by SDS-PAGE for HMW-GS 1Ax1 to determine if cosegregation had occurred.

EXAMPLE 7

Segregation Analysis, Stability of Coexpression, and Level of HMW-GS Accumulation Mature embryos excised from 20 R1 and 120–240 R2 seeds of each line (6 to 12 plants/line) were germinated on the bialaphos containing B3 medium, to study segregation and expression of the transgene bar in successive generations, and to identify plants homozygous for bar. Germination frequencies of 16 lines did not differ significantly from Mendelian segregation for a single integration-site; lines 25 and 87 did not show Mendelian segregation (Table 1). PAT expression was lost in R1 plants of lines 62 and 228. Line 85, that carried but did not express the bar gene in R0, did not germinate on BS medium. Thus far, seven lines homozygous for PAT expression have been identified in the R2 generation. Coexpression/segregation of the 1Ax1 gene in these seven lines has been confirmed by SDS-PAGE analysis. Line 85, although not showing PAT activity, was found to accumulate HMW-GS 1Ax1 ; its homozygous progeny has also been identified. In two of the lines (line 87 and 235), an extra polypeptide (195 kDa and 156 kDa, respectively) of unknown origin that migrated slower than the transgenic HMW-GS 1Ax1, was seen (FIGS. 1, 2); this polypeptide was also present in subsequent generations. FIG. 1 (lanes 28–235) illustrates the differences in the level of accumulation of HMW-GS 1Ax1 between nine different lines. Densitometric scans of gels showed that the amount of HMW-GS 1Ax1 protein produced in the different lines varied from 0.6 to 2.3% of the total protein (Table 2). In the lines (28, 87, 159) showing the strongest expression, 32 to 40% of the total HMW-GS was comprised of the transgenic HMW-GS 1Ax1, without any decrease in the native HMW-GS, resulting in a 1.53- to 1.71-fold higher level of HMW-GS in R1 and R2 seeds, as well as in R3 seeds of line 159, compared to the nontransformed control (Table 2). The accumulation of HMW-GS 1Ax1 within the homozygous lines was uniform (FIG. 3). The differences in the relative amounts of HMW-GS 1Ax1 between different lines were largely consistent over successive generations.

TABLE 1

Germination ratios of mature embryos from R1 seeds on B3 medium (3 mg/l bialaphos)

| Transgenic line number | Germinated embryos | Nongerminated embryos | Germination ratio (%) |
| --- | --- | --- | --- |
| 25 | 11 | 9 | 55 |
| 28 | 16 | 4 | 80[a] |
| 29 | 16 | 4 | 80[a] |
| 30 | 16 | 4 | 80[a] |
| 31 | 15 | 5 | 75[a] |
| 51 | 13 | 7 | 65[a] |
| 62 | 0 | 20 | 0 |
| 70 | 16 | 4 | 80[a] |
| 85 | 0 | 20 | 0 |
| 87 | 4 | 16 | 25 |
| 134 | 17 | 3 | 85[a] |
| 136 | 15 | 5 | 75[a] |
| 138 | 14 | 6 | 70[a] |
| 153 | 15 | 5 | 75[a] |
| 159 | 16 | 4 | 80[a] |
| 213 | 14 | 6 | 70[a] |
| 217 | 16 | 4 | 80[a] |
| 228 | 0 | 20 | 0 |
| 229 | 17 | 3 | 85[a] |
| 233 | 14 | 6 | 70[a] |
| 235 | 15 | 5 | 75[a] |

[a]Analysis using the $\chi^2$ test indicated that segregation ratios of R1 mature embryos from these lines were not significantly different from 3:1 (at a = 0.005).

TABLE 2

Densitometric analysis of HMW-GS 1Ax1 gene expression in SDS-PAGE gels of total extractable proteins from R1, R2, and R3 seeds of individual wheat lines

| Line No. | Transgenic HMW-GS 1Ax1/ total extracted protein (%)[1] | | | Transgenic HMW-GS 1Ax1/total HMW-GS (%)[2] | | | Total HMW-GS as % of the control[3] | | |
| --- | --- | --- | --- | --- | --- | --- | --- | --- | --- |
| | R1 | R2 | R3 | R1 | R2 | R3 | R1 | R2 | R3 |
| 28 | 1.9 | 2.0 | n.a. | 32 | 34 | n.a. | 161 | 171 | n.a. |
| 29 | 1.3 | 1.0 | n.a. | 23 | 17 | n.a. | 132 | 159 | n.a. |
| 31 | 0.9 | 1.2 | n.a. | 23 | 22 | n.a. | 106 | 160 | n.a. |
| 85 | 0.6 | 0.6 | n.a. | 19 | 18 | n.a. | 92 | 104 | n.a. |
| 87 | 2.0 | 1.8 | n.a. | 35 | 32 | n.a. | 159 | 169 | n.a. |
| 159 | 2.0 | 2.2 | 2.3 | 36 | 39 | 40 | 153 | 168 | 165 |
| 217 | 1.4 | 0.9 | n.a. | 29 | 21 | n.a. | 135 | 114 | n.a. |
| 233 | 1.2 | 0.8 | n.a. | 29 | 24 | n.a. | 114 | 88 | n.a. |
| 235 | 0.6 | 0.6 | 0.6 | 14 | 16 | 15 | 116 | 110 | 114 |

The values given for R2 and R3 generations are averages of two gels, shown in FIGS. 1 and 2.
[1,2]The transgenic HMW-GS 1Ax1 peak was divided by the total value for the whole lane [1], or the sum of all HMW-GS peaks of the lane[2].
[3]The sum of all HMW-GS peak values divided by the value for the control lane (Bob White nontransformed) after normalizing the amount of protein. All values shown are after background correction of the individual HMW-GS 1Ax1, HMW-GS, or total protein peaks.
n.a. = not available at the time of analysis.

EXAMPLE 8

Southern Analysis

Southern blots of control nontransformed genomic DNA, digested with XbaI, showed two cross-reacting bands of 7.0 and 9.3 kb, after hybridization with a probe made from either the full length or the smaller coding region of the pHMW1Ax1 plasmid (control lanes of FIGS. 4, 5). The enzyme XbaI was used for DNA digestion because there is only one XbaI restriction site, outside the coding sequence, in pHMW1Ax1. Southern blots were made of genomic DNA from 12 transgenic lines (eight lines expressing 1Ax1, and four lines expressing only the bar gene but cotransformed with the plasmid pHMW1Ax1). After digestion with XbaI, six lines (28, 31, 85, 87, 233, 235) of the eight lines expressing 1Ax1 showed clear individual patterns of integration (FIGS. 4, 5), and the presence of multiple copies with irregular insertion and/or truncation of the plasmid. Two lines expressing 1Ax1 (159 and 217) showed an intense 7.0 kb band that comigrated with the endogenous band, but was much more intense than the second endogenous band of 9.3 kb. This suggests the presence of multiple copies in tandem concatemeric arrays. Among lines not expressing 1Ax1, line 25 clearly showed a pattern of integration that was similar to those of expressing lines 28 and 31. The transgene was not present in line 30, whereas lines 51 and 62 showed patterns that were very similar to that of the negative control plant, but with higher intensity. The integration of the transgene in the genomic DNA was demonstrated by comparing the hybridization of 1.0 μg of undigested DNA of four 1Ax1 expressing lines, and one nontransformed control plant (FIG. 5). The hybridization-signal in the expressing lines was clearly more intense than that of the negative control.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES CITED

Altpeter, F., Vasil V., Srivastava V., Stöger, E., Vasil I. K. (1996) "Accelerated production of transgenic wheat (*Triticum aestivum* L.) plants," *Plant Cell Rep.* (in press).

Blechl, A. E., Anderson, O. D. (1996) "Expression of a novel high molecular weight glutenin subunit gene in transgenic wheat," *Nature Biotechnology* 14:875–879.

Branlard, G. (1987) "Prediction of bread wheat quality from HMW glutenins and gliadins," In: Lasnity, R., and Bekes, F. (eds.), Proc. 3rd Internat. Workshop on Gluten Proteins, pp. 604–612. World Scientific, Singapore.

Christensen, A. H., Quail, P. H. (1996) "Ubiquitin promoter-based vectors for high level expression of selectable and/or screenable marker genes in monocotyledonous plants," *Transgen. Res.* 5:213–218.

Christou, P., Swain, W. F., Yang, N. S., McCabe, D. E. (1989) "Inheritance and expression of foreign genes in transgenic soybean plants," *Proc. Natl. Acad. Sci. USA* 86:7500–7504.

Flavell, R. B., Goldsbrough, A. P., Robert, L. S., Schnick, D., Thompson, R. D. (1989) "Genetic variation in wheat HMW glutenin subunits and the molecular basis of bread-making quality," *Bio/Technology* 7:1281–1285.

Halford, N. G., Field, J. M., Blair, H., Urwin, P., Moore, K., Robert, L., Thompson, R., Flavell, R. B., Tatham, A. S., Shewry, P. R. (1992) "Analysis of EMW glutenin subunits encoded by chromosome 1A of bread wheat *Triticum aestivum* L.) indicates quantitative effects on grain quality," *Theoret. Appl. Genet.* 83:373–378.

Laemmli, U. K. (1970) "Cleavage of structural proteins during the assembly of the head of bacteriophage T4," *Nature* 227:680–685.

Lassner, M. W., Peterson, P., Yoder, J. I. (1989) "Simultaneous amplification of multiple DNA fragments by polymerase chain reaction in the analysis of transgenic plants and their progeny," *Plant Molec. Biol. Rep.* 7:116–128.

Murashige, T., and Skoog, F. (1962) "A revised medium for rapid growth and bioassays with tobacco tissue cultures," *Physiol. Plant* 15:473–497.

Neuhoff, V., Arnold, N., Taube, D., Ehrhardt, W. (1988) "Improved staining of proteins in polyacrylamide gels including isoelectric focusing gels with clear background at nanogram sensitivity using Coomassie Brilliant Blue U-250 and R-250," *Electrophoresis* 9:255–262.

Payne, P. I., Corfield, K. C., Blackman, J. A. (1979) "Identification of a high molecular weight subunit of glutenin whose presence correlates with breadmaking quality in wheats of related pedigree," *Theoret. Appl. Genet.* 55:153–159.

Payne, P. I., Corfield, K. G., Holt, L. M., Blackman, J. A. (1981) "Correlations between the inheritance of certain high molecular weight subunits of glutenin and bread-making quality in progenies of six crosses of bread wheat," *J. Food Sci. Agric.* 32:51–60.

Payne, P. I. (1987) "Genetics of wheat storage proteins and the effect of allelic variation on breadmaking quality," *Annu. Rev. Plant Physiol.* 38:141–153.

Seilmeier, W., Belitz, H. -D., Wieser, H. (1991) "Separation and quantitative determination of high-molecular-weight subunits of glutenin from different wheat varieties and genetic variants of the variety Sisco," *Z. Lebensm. Unters. Forsch.* 192:124–129.

Shewry, P. R., Tatham, A. S., Barro, F., Barcelo, P., Lazzeri, P. (1995) "Biotechnology of breadmaking: unraveling and manipulating the multi-protein gluten complex," *Biotechnology* 13:1185–1190.

Shewry, P. R. (1995) "Plant storage proteins," *Biol. Rev.* 70:375–426.

Spencer, T. M., Gordon-Kamm, W. J., Daines, R. J., Start, W. G., Lemaux, P. G. (1990) "Bialaphos selection of stable transformants from maize cell culture," *Theoret. Appl. Genet.* 79:625–631.

Spencer, T. M., O'Brien, J. V., Start, W. C., Adams, T. R., Gordon-Kamm, W.J., Lemaux, P. O. (1992) "Segregation of transgenes in maize," *Plant Molec. Biol.* 18:20–210.

Srivastava, V., Vasil, V., Vasil, I. K. (1996) "Molecular characterization of the fate of transgenes in transformed wheat (*Triticum aestivum* L.)," *Theoret. Appl. Genet.* 92:1031–1037.

Taylor, M. G., Vasil, V., Vasil, I. K. (1993) "Enhanced GUS gene expression in cereal/grass cell suspensions and immature embryos using the maize ubiquitin-based plasmid pAHC25," *Plant Cell Rep.* 12:491–495.

Vasil, I. K. (1994) "Molecular improvement of cereals," *Plant Molec. Biol.* 25:925–937.

Vasil, V., Srivastava, V., Castillo, A. M., Fromm, M. E., Vasil, I. K. (1993) "Rapid production of transgenic wheat plants by direct bombardment of cultured immature embryos," *BiolTechnology* 11:1553–1558.

Wrigley, C. W. (1996) "Giant proteins with flour power," *Nature* 381:738–739.

We claim:

1. A method for producing a plant with improved breadmaking characteristics comprising the steps of:

(a) transforming a wheat cell to contain a heterologous DNA segment encoding a protein and derived from a wheat HMW-GS 1Ax1 polynucleotide not native to said cell; wherein said polynucleotide is operably linked to a promoter that can be used effectively for expression of transgenic proteins in the endosperm tissue;

(b) growing and maintaining said cell under conditions whereby a transgenic wheat plant is regenerated therefrom;

(c) growing said transgenic plant under conditions whereby said DNA is expressed, whereby the total amount of HMW-GS in seeds of said wheat plant is increased, resulting in improving the breadmaking characteristics of flour produced from said seeds.

2. The method of claim 1, further comprising the step of obtaining and growing additional generations of descendants of said transgenic plant which comprise said heterologous DNA segment wherein said heterologous DNA segment is expressed.

3. The method of claim 1 wherein said heterologous DNA segment comprises the 1Ax1 promoter.

4. The method of claim 2 wherein said DNA segment comprises the 1Ax1 promoter.

5. The method of claim 1 wherein said heterologous DNA segment is expressed under the control of the 1Ax1 promoter.

6. The method of claim 2 wherein said heterologous DNA segment is expressed under the control of the 1Ax1 promoter.

7. The method of claim 1, whereby said transformed wheat cell comprises at least six DNA segments each of which encodes a different wheat HMW-GS protein, and whereby said transgenic wheat plant comprises cells wherein at least six of said DNA segments are expressed, whereby said cells contain at least six different HMW-GS proteins.

8. The method of claim 7, further comprising the step of obtaining and growing additional generations of descendants of said transgenic plant which comprise said heterologous DNA segment wherein said heterologous DNA segment is expressed.

9. The method of claim 7 wherein said heterologous DNA segment comprises the 1Ax1 promoter.

10. The method of claim 8 wherein said DNA segment comprises the 1Ax1 promoter.

11. The method of claim 7 wherein said heterologous DNA segment is expressed under the control of the 1Ax1 promoter.

12. The method of claim 8 wherein said heterologous DNA segment is expressed under the control of the 1Ax1 promoter.

13. The method of claim 1, wherein said heterologous DNA segment encodes the 1Ax1 protein.

14. The method of claim 2, wherein said heterologous DNA segment encodes the 1Ax1 protein.

15. The method of claim 3, wherein said heterologous DNA segment encodes the 1Ax1 protein.

16. The method of claim 4, wherein said heterologous DNA segment encodes the 1Ax1 protein.

17. The method of claim 5, wherein said heterologous DNA segment encodes the 1Ax1 protein.

18. The method of claim 6, wherein said heterologous DNA segment encodes the 1Ax1 protein.

19. The method of claim 7, wherein said heterologous DNA segment encodes the 1Ax1 protein.

20. The method of claim 8, wherein said heterologous DNA segment encodes the 1Ax1 protein.

21. The method of claim 9, wherein said heterologous DNA segment encodes the 1Ax1 protein.

22. The method of claim 10, wherein said heterologous DNA segment encodes the 1Ax1 protein.

23. The method of claim 11, wherein said heterologous DNA segment encodes the 1Ax1 protein.

24. The method of claim 12, wherein said heterologous DNA segment encodes the 1Ax1 protein.

25. A method for producing a plant with improved breadmaking characteristics comprising the steps of:

(a) transforming a wheat cell with a wheat 1Ax1 polynucleotide; wherein said polynucleotide is operably linked to a promoter that can be used effectively for expression of transgenic proteins in the endosperm tissue;

(b) growing and maintaining said cell under conditions whereby a transgenic wheat plant is regenerated therefrom;

(c) growing said transgenic plant under conditions whereby said DNA is expressed, whereby the total amount of HMW-GS in seeds of said wheat plant is increased, resulting in improving the breadmaking characteristics of flour produced from said seeds.

* * * * *

UNITED STATES PATENT AND TRADEMARK OFFICE
CERTIFICATE OF CORRECTION

PATENT NO. : 6,252,134 B1
DATED : June 26, 2001
INVENTOR(S) : Indra K. Vasil and Vimla Vasil It is certified that error appears in the above-identified patent and that said Letters Patent is hereby corrected as shown below:

Column 1,
Line 50, "1 Ay" should read -- 1 Ay --.

Column 2,
Line 19, "bombardmentof" should read -- bombardment of --.

Column 3,
Line 46, "et aL." should read -- et al. --.

Column 5,
Line 25, "withpAHC25" should read -- with $p$AHC25 --.

Column 8,
Lines 59-60, "hybridization-signal" should read -- hybridization signal --.

Column 10,
Line 20, "Bio1Technology" should read -- Bio/Technology --.

Signed and Sealed this

Sixth Day of August, 2002

Attest:

JAMES E. ROGAN
Attesting Officer       Director of the United States Patent and Trademark Office